United States Patent [19]

Delbressine et al.

[11] Patent Number: 5,763,476
[45] Date of Patent: Jun. 9, 1998

[54] SUBLINGUAL OR BUCCAL PHARMACEUTICAL COMPOSITION

[75] Inventors: Leonardus Petrus Carla Delbressine, Nijmegen; Johannes Hubertus Wieringa, Heesch, both of Netherlands

[73] Assignee: Akzo Noble N.V., Arnhem, Netherlands

[21] Appl. No.: 693,064

[22] PCT Filed: Mar. 1, 1995

[86] PCT No.: PCT/EP95/00765

§ 371 Date: Oct. 11, 1996

§ 102(e) Date: Oct. 11, 1996

[87] PCT Pub. No.: WO95/23600

PCT Pub. Date: Sep. 8, 1995

[30] Foreign Application Priority Data

Mar. 2, 1994 [EP] European Pat. Off. .............. 94200521

[51] Int. Cl.$^6$ .................................................. A61K 31/40
[52] U.S. Cl. .......................... 514/410; 514/270; 514/289; 514/315; 514/318
[58] Field of Search ............................. 424/274; 514/410, 514/206, 270, 289, 315, 318

[56] References Cited

FOREIGN PATENT DOCUMENTS

| 0569096 | 11/1993 | European Pat. Off. . |
| 0578823 | 1/1994 | European Pat. Off. . |
| 2366835 | 5/1978 | France . |

OTHER PUBLICATIONS

Handbook of Pharmaceutical Excipients, ISBN (US): 0-917330-56-0, Published 1986, pp. 119–120.

*Primary Examiner*—Keith D. MacMillan
*Attorney, Agent, or Firm*—Sharon N. Klesner; Mary E. Gormley

[57] ABSTRACT

The invention relates to a sublingual or buccal pharmaceutical composition comprising trans-5-chloro-2-methyl-2,3,3a,12b-tetrahydro-1H-dibenz[2,3:6,7]oxepino-[4,5-c]pyrrole or a pharmaceutically acceptable salt thereof, and pharmaceutically acceptable auxiliaries suitable for use in sublingual or buccal compositions, and the use thereof for the manufacture of a sublingual or buccal pharmaceutical composition for the treatment of mental disorders, such as psychosis and schizophrenia.

13 Claims, No Drawings

SUBLINGUAL OR BUCCAL PHARMACEUTICAL COMPOSITION

This application is a 371 of PCT/EP95/00765, filed Mar. 1, 1995.

The invention relates to a sublingual or buccal pharmaceutical composition, and more specifically to a sublingual or buccal composition for the treatment of various mental disorders.

The compound trans-5-chloro-2-methyl-2,3,3a,12b-tetrahydro-1H-dibenz[2,3:6,7]oxepino[4,5-c]pyrrole and the preparation thereof are disclosed in U.S. Pat. No. 4,145,434. The compound is described as having CNS-depressant activity and antihistamine and antiserotonin activities.

The pharmacological profile of trans-5-chloro-2-methyl-2,3,3a,12b-tetrahydro-1H-dibenz[2,3:6,7]oxepino[4,5-c]pyrrole, its kinetics and metabolism, as well as the first safety and efficacy studies in human volunteers and in schizophrenic patients were reviewed by De Boer et al. (Drugs of the Future 1993, 18(12), 1117–1123). It has been established that Org 5222 [5-chloro-2-methyl-2,3,3a,12b-tetrahydro-1H-dibenz[2,3:6,7]oxepino[4,5-c]pyrrole maleate (1:1)] is a very potent dopamine and serotonin antagonist with potential antipsychotic activity.

Phase I clinical studies on the effects of perorally administered trans-5-chloro-2-methyl-2,3,3a,12b-tetrahydro-1H-dibenz[2,3:6,7]oxepino[4,5-c]pyrrole however, revealed that serious cardiotoxic effects, e.g. postural hypotension and/or impairment of baroreceptor functioning, occurred.

Surprisingly, it has now been found that on sublingual or buccal administration, trans-5-chloro-2-methyl-2,3,3a,12b-tetrahydro-1H-dibenz[2,3:6,7]oxepino[4,5-c]pyrrole has substantially less cardiovascular side effects.

The invention therefore relates to a sublingual or buccal pharmaceutical composition comprising trans-5-chloro-2-methyl-2,3,3a,12b-tetrahydro-1H-dibenz-[2,3:6,7]oxepino[4,5-c]pyrrole or a pharmaceutically acceptable salt thereof, and pharmaceutically acceptable auxiliaries suitable for use in sublingual or buccal compositions.

The compositions of the invention are useful in treating mammals, including humans, suffering from diseases which are susceptible to treatment by trans-5-chloro-2-methyl-2,3,3a,12b-tetrahydro-1H-dibenz[2,3:6,7]oxepino[4,5-c]pyrrole. Such diseases include mental disorders, such as tension, excitation, anxiety, psychosis, and schizophrenia. The compositions may also be used for antihistamine and for antiserotonin related diseases.

In its simplest form the pharmaceutical composition of the invention consists of an aqueous solution, for instance comprising 0.9% (w/v) of sodium chloride and the active compound 5-chloro-2-methyl-2,3,3a,12b-tetrahydro-1H-dibenz[2,3:6,7]oxepino[4,5-c]pyrrole, or a pharmaceutically acceptable salt thereof. The maleate salt (Org 5222) is a preferred salt. The active compound is rapidly absorbed from these aqueous pharmaceutical compositions, when kept under the tongue or in the mouth of a patient.

Preferred pharmaceutical compositions are solid pharmaceutical compositions which rapidly disintegrate in the mouth of a subject, upon insertion into the buccal pouch or upon placement under the tongue. Rapid disintegration means that the pharmaceutical composition is disintegrated within 30 seconds in water at 37° C., and preferably within 10 seconds, as measured according to the procedure described in Remington's Pharmaceutical Sciences, 18th Edition (Ed. A. R. Genaro), 1990, pp 1640–1641; see also US Pharmacopeia, Chapter <701>.

In a preferred embodiment the pharmaceutical compositions of the invention are tablets or lozenges which comprise a rapidly disintegrating composition of a pharmaceutically acceptable water-soluble or water-dispersable carrier material. Tablets and lozenges comprising a rapidly disintegrating composition of a pharmaceutically acceptable water-soluble or water-dispersable carrier material are known in the art, for example as disclosed in U.S. Pat. No. 4,371,516. Such tablets may be prepared by freeze-drying of an aqueous solution comprising 5-chloro-2-methyl-2,3,3a,12b-tetrahydro-1H-dibenz[2,3:6,7]oxepino[4,5-c]pyrrole, a water-soluble or water-dispersable carrier material and, optionally, pharmaceutically acceptable excipients. Such excipients are known in the art, see for instance Remington's Pharmaceutical Sciences, 18th Edition (Ed. A. R. Genaro), 1990, pp 1635–1638, and are commonly used in pharmaceutical compositions, for instance surfactants, colouring agents, flavouring agents, preservatives and the like.

The water-soluble or water-dispersable carrier material is preferably water-soluble. Suitable water-soluble carrier materials are (poly)saccharides like hydrolysed dextran, dextrin, mannitol, and alginates, or mixtures thereof, or mixtures thereof with other carrier materials like polyvinylalcohol, polyvinylpyrrolidine and water-soluble cellulose derivatives, like hydroxypropyl cellulose.

A preferred carrier material is gelatin, especially partially hydrolysed gelatin. The partially hydrolysed gelatin can be prepared by heating of a solution of gelatin in water, for example in an autoclave at about 120° C. for up to 2 hours. The hydrolysed gelatin is used in concentrations of about 1 to 6% (w/v), and preferably in concentrations of about 2 to 4% (w/v).

The preferred dosage forms of the composition of the invention, i.e. tablets or lozenges, can be prepared by methods known in the art. For example, according to a method as disclosed in British Patent 2,111,423, an aqueous composition comprising a predetermined amount of 5-chloro-2-methyl-2,3,3a,12b-tetrahydro-1H-dibenz-[2,3:6,7]oxepino[4,5-c]pyrrole, a pharmaceutically acceptable water-soluble or water-dispersable carrier material and optionally pharmaceutically acceptable auxiliaries and excepients, is transferred into a mould, after which the composition is frozen and the solvent is sublimed, preferably by freeze-drying. The composition preferably contains a surfactant, for example Tween 80 (polyoxyethylene (20) sorbitan mono-oleate), which may help to prevent the freeze-dried product from sticking to the surface of the mould.

The mould may comprise a series of cylindrical or other shape depressions, each having a size corresponding to the desired size of the dosage form. Alternatively, the mould may have a larger size than the desired size of the dosage form, and after the contents are freeze-dried the product can be cut into the desired size. Preferably the dosage form is freeze-dried in the form of a lyosphere, which is a freeze-dried spherical-shaped droplet containing the active ingredient.

A preferred mould would correspond to a depression in a sheet of film material, as for example disclosed in U.S. Pat. No. 4,305,502 and U.S. Pat. No. 5,046,618. The film material may be similar to that employed in conventional blister packs.

Each dosage form of the pharmaceutical composition of the present invention comprises one dosage unit of 5-chloro-2-methyl-2,3,3a,12b-tetrahydro-1H-dibenz-[2,3:6,7]oxepino[4,5-c]pyrrole as active ingredient. A dosage unit may contain between 0.005 mg and 15 mg of the active ingredient. Preferably the dosage unit contains 0.03–0.50 mg of 5-chloro-2-methyl-2,3,3a,12b-tetrahydro-1H-dibenz[2,3:6,7]oxepino[4,5-c]pyrrole.

The invention further relates to the use of trans-5-chloro-2-methyl-2,3,3a,12b-tetrahydro-1H-dibenz-[2,3:6,7] oxepino[4,5-c]pyrrole for the manufacture of a sublingual or buccal pharmaceutical composition for treating mental disorders, such as psychosis and schizophrenia.

A method of providing therapy using the pharmaceutical composition of the present invention comprises the insertion of a dosage form according to this invention in the buccal pouch or under the tongue of a subject, such as a human. The ultimate dosage to provide relief for the patient depends, apart from individual characteristics, on the patient's weight, condition and age. Usually, administration of 1–4 dosage units of the pharmaceutical composition of the invention per day is sufficient for obtaining a therapeutic effect. The therapy may be continued as long as necessary or desired.

The invention is further illustrated by the following examples.

Example 1 a: Preparation of Hydrolysed Gelatin (3% w/v)

Gelatin (30 g) was dissolved in 1 l of distilled water under heating and constant stirring. The resulting solution was autoclaved at 121° C. ($10^5$ Pa) for one hour, upon which the solution was allowed to cool to room temperature to give hydrolysed gelatin (3% w/v).

b: Preparation of a Solid Pharmaceutical Dosage Form

A sheet of polyvinyl chloride (PVC) containing cylindrical depressions was cooled with solid carbon dioxide. 0.2 g of Org 5222 [5-chloro-2-methyl-2,3,3a,12b-tetrahydro-1H-dibenz[2,3:6,7]oxepino[4,5-c]pyrrole maleate (1:1)] were dissolved in 1 l of hydrolysed gelatin under mixing. While mixing was continued, in each of the depressions 0.5 ml of the solution were placed. When the contents of the depressions were frozen, the PVC sheet was placed in a freeze-drying system. An aluminum foil was finally sealed to the sheet so as to close off the depressions containing the freeze-dried pharmaceutical dosage forms. Each depression contains a pharmaceutical unit dosage comprising 0.10 mg of 5-chloro-2-methyl-2,3,3a,12b-tetrahydro-1H-dibenz[2,3:6,7]oxepino[4,5-c]pyrrole maleate (1:1).

Examples 2

In a manner as described in Example 1b a pharmaceutical composition was prepared comprising:

0.2 g of 5-chloro-2-methyl-2,3,3a,12b-tetrahydro-1H-dibenz[2,3:6,7]oxepino[4,5-c]pyrrole maleate (1:1) (Org 5222), 0.50 g of Tween 80 (polyoxyethylene (20) sorbitan mono-oleate, 30 g of sucrose and 1 l of hydrolysed gelatin (3% w/v).

Example 3

In a manner as described in Example 1b a pharmaceutical composition was prepared comprising:

2 g of 5-chloro-2-methyl-2,3,3a,12b-tetrahydro-1H-dibenz[2,3:6,7]oxepino[4,5-c]pyrrole maleate (1:1) (Org 5222), 0.50 g of Tween 80 (polyoxyethylene (20) sorbitan mono-oleate, 30 g of sucrose and 1 l of hydrolysed gelatin (3% w/v), 1 l of hydrolysed gelatin (3% w/v).

Example 4

A pharmaceutical composition was prepared comprising:

0.2 g of 5-chloro-2-methyl-2,3,3a,12b-tetrahydro-1H-dibenz[2,3:6,7]oxepino[4,5-c]pyrrole maleate (1:1) (Org 5222), 17 g of sodium alginate, 35 g of dextran (MW approx. 40.000), 17.5 g of dextrose, and distilled water to a volume of 1 l, which composition was freeze-dried into unit dosage forms.

Example 5

A pharmaceutical composition was prepared comprising:

0.4 g of 5-chloro-2-methyl-2,3,3a,12b-tetrahydro-1H-dibenz[2,3:6,7]oxepino[4,5-c]pyrrole maleate (1:1) (Org 5222), 50 g of dextrin, 0.20 g of Tween 80 (polyoxyethylene (20) sorbitan mono-oleate, 30 g of polyvinylpyrrolidine and distilled water to a volume of 1 l, which composition was freeze-dried into unit dosage forms.

Example 6

Lyospheres were prepared by dissolving 138.9 g of sucrose, 40.8 g of sodium citrate, and 111 mg of polysorbate 20 in 300 ml of distilled water, adjusting the pH to 7 using 1N hydrochloric acid and 1N sodium hydroxide and adding water to 500 ml. The solution was homogenized by stirring and filtered through a sterile 0.22 μm filter, after which the solution was freezed into droplets of 0.1 ml, which droplets were transferred in the frozen state into a freeze dryer and then freeze-dried to unloaded spherical lyophilized dosage units (lyospheres).

120 mg of 5-chloro-2-methyl-2,3,3a,12b-tetrahydro-1H-dibenz[2,3:6,7]oxepino[4,5-c]pyrrole maleate (1:1) (Org 5222) were dissolved in 1 ml of ethanol and 83 μl of this solution were added to one lyospheres, after which the ethanol was removed by gentle heating, to obtain a lyosphere containing 10 mg of Org 5222. Lyospheres containing 1 and 0.1 mg of Org 5222 respectively, were prepared in a similar manner by dissolving 60 or 6 mg of Org 5222 respectively in 1 ml of ethanol, after which 16.6 μl of this solution were added to one lyosphere.

Example 7

A pharmaceutical composition was prepared comprising:

0.094 g of 5-chloro-2-methyl-2,3,3a,12b-tetrahydro-1H-dibenz[2,3:6,7]oxepino[4,5-c]pyrrole maleate (1:1) (Org 5222), 30 g of mannitol, 40 g of gelatine, and distilled water to a volume of 1 l, which composition was freeze-dried according to the method of Example 1b into unit dosage forms, each of which comprises 10 μg of Org 5222.

Example 8

Orthostatic hypotension (tilt challenge) and direct haemodynamic and electrophysiologic effects were determined as follows:

Method

Beagle dogs (10–20 kg, Harlan, France) were instrumented under anesthesia. A micromanometer (Konigsberg Instruments) was placed into the aorta near the aortic arch and another in the left ventricle. A pair of segment length piezoelectric crystals (Triton Technology) were sutured into the endocardial left ventricular wall at a distance of approximately 1 cm from each other. All connecting wires were tunneled subcutaneously and exteriorized at the back of the neck. Two weeks postoperatively the dogs were placed in a Pavlov-stand and transducers connected to an eight-channel recorder (Gould ES3000). An electrocardiogram (standard lead II) was also recorded using conventional bipolar limb leads.

Org 5222 (or placebo) was administered either orally (1, 2.5, 5, 10, or 50 mg/kg) or sublingually (0.01, 0.1, or 1 mg/kg) to conscious dogs.

Aortic arterial systolic, diastolic and mean blood pressures (mmHg), heart rates (beats/min), ventricular systolic segmental shortenings (mm) and the QT intervals were continuously registered and automatically analysed every 15 minutes during the 5 hour observation period following Org 5222 administration. QTc (which reflects cardiac repolarisation time) was calculated according to Bazett's formula.

Dogs were tilted to the 90° upright position for periods of 30 seconds by lifting their forelimbs. Tilt responses refer to the maximum changes observed in aortic blood pressure and heart rate during the 30 second observation period and were assessed both 30 minutes and just before Org 5222 administration and then 15, 30, 60, 90, 120, 180, 240, and 300 minutes after administration.

Blood samples were taken just before drug administration and at 15, 30, 60, 90, 120, 240, 300, 360 minutes and at 21 hours after administration in each case just after tilt challenge. To plasma, prepared from the blood samples, internal standard (cis-5-chloro-2-methyl-2,3,3a,12b-tetrahydro-1H-dibenz[2,3:6,7]oxepino[4,5-c]pyrrole maleate (1:1); Org 5033) was added and Org 5222 and internal standard were isolated by extracting the alkalinized plasma with n-hexane. The Org 5222 concentration was determined by capillary gas chromatography (cGC) with NPD-detection.

Results

The hypotensive response to tilt was modestly and dose-dependently augmented by Org 5222, irrespective of the route of administration. However, for equivalent Org 5222 plasma levels, the accompanying tachycardia was always more marked after oral administration of Org 5222 than after sublingual administration (Table 1)

TABLE 1

Mean heart rate change due to tilt
(corrected for placebo effects), calculated per
concentration range (ng/ml) and for each of the two
administration routes, oral (po) and sublingual (sl).

| Org 5222 plasma concentration | Mean heart rate change per concentration range | |
|---|---|---|
| (ng/ml) | po | sl |
| 0–3 | 5.7 | 4.6 |
| 3–10 | 21.3 | 0.6 |
| 10–30 | 21.1 | 18.3 |
| 30–100 | 47.8 | 14.9 |
| 100–300 | 52.8 | 8.9 |

Conclusions

Tachycardia accompanying orthostatic hypotension was more marked after oral than after sublingual administration of Org 5222. Direct haemodynamic and electrophysiological effects were also less marked after sublingual than after oral administration with regard to negative inotropy and QTc prolongation.

Moreover, dogs treated orally showed marked side effects such as excitation of long duration, whereas dogs treated sublingually showed only short excitation periods followed by long lasting sedation.

We claim:

1. A pharmaceutical composition comprising as a medicinally active compound: trans-5-chloro-2-methyl-2,3,3a,12b-tetrahydro-1H-dibenz[2,3:6,7]oxepino[4,5-c]pyrrole or a pharmaceutically acceptable salt thereof; wherein the composition is a solid composition and disintegrates within 30 seconds in water at 37° C.

2. The pharmaceutical composition of claim 1, wherein the composition further comprises a pharmaceutically acceptable water-soluble or water-dispersable carrier material.

3. The pharmaceutical composition of claim 2, wherein the carrier material is partially hydrolysed gelatin.

4. A method for treating tension, excitation, anxiety, and psychotic and schizophrenic disorders, comprising administering sublingually or buccally an effective amount of a pharmaceutical composition comprising trans-5-chloro-2-methyl-2,3,3a,12b-tetrahydro-1H-dibenz[2,3:6,7]oxepino[4,5-c]pyrrole or a pharmaceutically acceptable salt thereof.

5. The pharmaceutical composition of claim 1, wherein the composition disintegrates within 10 seconds in water at 37° C.

6. The composition of claim 1, further comprising one or more pharmaceutically acceptable auxiliaries selected from the group consisting of hydrolyzed dextran, dextrin, mannitol, algenates, polyvinyl alcohol, polyvinyl pyrrolidine and water soluble cellulose derivatives.

7. A pharmaceutical composition comprising trans-5-chloro-2-methyl-2,3,3a,12b-tetrahydro-1H-dibenz[2,3:6,7]oxepino[4,5-c]pyrrole or a pharmaceutically acceptable salt thereof; and pharmaceutically acceptable auxiliaries, wherein the composition is made by the process of a) providing an aqueous solution comprising said compound and a water soluble or water dispersable carrier material;

b) transferring the composition of a) into a mold;

c) freezing the composition in the mold; and d) subliming the solvent by freeze-drying.

8. A pharmaceutical composition comprising trans-5-chloro-2-methyl-2,3,3a,12b-tetrahydro-1H-dibenz[2,3:6,7]oxepino[4,5-c]pyrrole maleate, mannitol, and gelatin.

9. The method of claim 4, wherein the composition is a solid pharmaceutical composition which rapidly disintegrates in the mouth of a subject upon insertion into the buccal pouch or upon placement under the tongue.

10. The method of claim 4, wherein the pharmaceutical composition further comprises pharmaceutically acceptable auxiliaries selected from the group consisting of hydrolyzed dextran, dextrin, mannitol, algenates, polyvinyl alcohol, polyvinyl pyrrolidine and water soluble cellulose derivatives.

11. The method of claim 10, wherein the pharmaceutically acceptable auxiliary is partially hydrolyzed gelatin.

12. The method of claim 4 wherein the pharmaceutical composition comprises trans-5-chloro-2-methyl-2,3,3a,12b-tetrahydro-1H-dibenz[2,3:6,7]oxepino[4,5-c]pyrrole maleate, mannitol, and gelatin.

13. A method for treating antihistamine and antiserotonin related diseases comprising administering sublingually or buccally an effective amount of a pharmaceutical composition comprising trans-5-chloro-2-methyl-2,3,3a,12b-tetrahydro-1H-dibenz[2,3:6,7]oxepino[4,5-c]pyrrole or a pharmaceutically acceptable salt thereof.

* * * * *

UNITED STATES PATENT AND TRADEMARK OFFICE
CERTIFICATE OF CORRECTION

PATENT NO. : 5,763,476
DATED : June 9, 1998
INVENTOR(S) : Delbressine et al.

It is certified that error appears in the above-identified patent and that said Letters Patent is hereby corrected as shown below:

Title page, in the "[73] Assignee" section, please delete "Akzo Noble" and replace with -- Akzo Nobel --.

Signed and Sealed this

Twenty-fourth Day of November, 1998

Attest:

BRUCE LEHMAN

Attesting Officer     Commissioner of Patents and Trademarks